United States Patent
Chisholm et al.

(10) Patent No.: US 7,227,048 B2
(45) Date of Patent: Jun. 5, 2007

(54) CONVERTING OXYGENATES TO OLEFINS OVER A CATALYST COMPRISING ACIDIC MOLECULAR SIEVE OF CONTROLLED CARBON ATOM TO ACID SITE RATIO

(75) Inventors: Paul N. Chisholm, Houston, TX (US); Nicolas P. Coute, Houston, TX (US); James R. Lattner, Seabrook, TX (US); Teng Xu, Houston, TX (US); Jeffrey S. Smith, Seabrook, TX (US); Keith Holroyd Kuechler, Friendswood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 595 days.

(21) Appl. No.: 10/227,907

(22) Filed: Aug. 26, 2002

(65) Prior Publication Data
US 2003/0125598 A1    Jul. 3, 2003

Related U.S. Application Data

(60) Provisional application No. 60/345,420, filed on Dec. 31, 2001.

(51) Int. Cl.
*C07C 1/20*    (2006.01)

(52) U.S. Cl. ........................... 585/639; 585/640
(58) Field of Classification Search ................ 585/639, 585/640
See application file for complete search history.

(56) References Cited

U.S. PATENT DOCUMENTS

| | | | |
|---|---|---|---|
| 4,440,871 A | 4/1984 | Lok et al. | |
| 4,547,616 A | 10/1985 | Avidan et al. | 585/640 |
| 4,873,390 A | 10/1989 | Lewis et al. | 585/638 |
| 6,023,005 A | 2/2000 | Lattner et al. | 585/639 |
| 6,137,022 A | 10/2000 | Kuechler et al. | 585/638 |

OTHER PUBLICATIONS

Bos et al. "Conversion of Methanol to Lower Olefins. Kinetic Modeling, Reactor Simulation, and Selection." *Ind. Eng. Chem. Res.* vol. 34, pp. 3808-3816, (1995).

(Continued)

*Primary Examiner*—Thuan Dinh Dang (57) ABSTRACT

The present invention provides a process for making an olefin product from an oxygenate-containing feedstock comprising:

a) contacting the feedstock in a reaction zone with catalyst particles comprising a molecular sieve containing acid sites and having an average coke loading of 1 to 10 carbon atoms per acid site of said molecular sieve, under conditions effective to convert the feedstock into an olefin product stream and to provide unregenerated catalyst particles, b) removing a portion of said catalyst particles from said reaction zone and contacting said portion with a regeneration medium in a regeneration zone under conditions effective to obtain regenerated catalyst particles which have an average coke loading of no greater than 10 carbon atoms per acid site of said molecular sieve, and c) introducing said regenerated catalyst particles into said reaction zone to provide a catalyst mixture of unregenerated catalyst particles and regenerated catalyst particles, in an amount sufficient to provide an average coke loading on said catalyst mixture in an amount ranging from 1 to 10 carbon atoms per acid site of said molecular sieve.

16 Claims, 3 Drawing Sheets

OTHER PUBLICATIONS

Soendararajan et al., "Modeling of Methanol to Olefins (MTO) Process in a Circulating Fluidized Bed Reactor," *Fuel*, vol. 80, pp. 1187-1197 (2001).

"Conversion of Methanol to Lower Olefins. Kinetic Modeling, Reactor Stimulation, and Selection," A.N. Rene Bos et al., Ind. Eng. Chem. Res., vol. 34, pp 3808-3816, 1995.

"Structural and chemical influences ont he MTO reaction: a comparison of chabazite and SAPO-34 as MTO catalysts," Ivar M. Dahl et al., Microporous and Mesoporous Materials, vol. 29, pp. 185-190, 1999.

"The characteristics of SAPO-34, which influence the conversion of methanol to light olefins," S. Wilson et al., Microporous and Mesoporous Materials, vol. 29, pp. 117-126, 1999.

"The effect of crystal size of SAPO-34 on the selectivity and deactivation of the MTO reaction," De Chen, et al., Microporous and Mesoporous Materials, vol. 29, pp. 191-203, 1999.

CONVERTING OXYGENATES TO OLEFINS OVER A CATALYST COMPRISING ACIDIC MOLECULAR SIEVE OF CONTROLLED CARBON ATOM TO ACID SITE RATIO

RELATED APPLICATIONS

This application is a non-provisional application claiming priority from, and incorporating by reference in its entirety, provisional U.S. Application Ser. No. 60/345,420, filed Dec. 31, 2001.

FIELD OF THE INVENTION

The present invention relates to a method for converting a feed including an oxygenate to a product including a light olefin.

BACKGROUND OF THE INVENTION

Light olefins, defined herein as ethylene, propylene, butylene and mixtures thereof, serve as feeds for the production of numerous important chemicals and polymers. Typically, light olefins are produced by cracking petroleum feeds. Because of the limited supply of competitive petroleum feeds, the opportunities to produce low cost light olefins from petroleum feeds are limited. Efforts to develop light olefin production technologies based on alternative feeds have increased.

An important type of alternate feed for the production of light olefins is oxygenate, such as, for example, alcohols, particularly methanol and ethanol, dimethyl ether, methyl ethyl ether, diethyl ether, dimethyl carbonate, and methyl formate. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for light olefin production.

The catalysts used to promote the conversion of oxygenates to olefins are molecular sieve catalysts. Because ethylene and propylene are the most sought after products of such a reaction, research has focused on what catalysts are most selective to ethylene and/or propylene, and on methods for increasing the life and selectivity of the catalysts to ethylene and/or propylene.

The conversion of oxygenates to olefins generates and deposits carbonaceous material (coke) on the molecular sieve catalysts used to catalyze the conversion process. Over accumulation of these carbonaceous deposits will interfere with the catalyst's ability to promote the reaction. In order to avoid unwanted build-up of coke on the molecular sieve catalyst, the oxygenate to olefin process incorporates a second step comprising catalyst regeneration. During regeneration, the coke is removed from the catalyst by combustion with oxygen, which restores the catalytic activity of the catalyst. The regenerated catalyst then may be reused to catalyze the conversion of oxygenates to olefins.

Typically, oxygenate to olefin conversion and regeneration are conducted in two separate vessels. The coked catalyst is continuously withdrawn from the reaction vessel used for conversion to a regeneration vessel and regenerated catalyst is continuously withdrawn from the regeneration vessel and returned to the reaction vessel for conversion.

U.S. Pat. No. 4,547,616 to Avidan et al., incorporated herein by reference, discloses a process for converting oxygenates to lower olefins by operating a fluidized bed of zeolite catalyst, e.g. ZSM-5, whose activity is controlled to produce a product having propane:propene molar ratio ranging from 0.04:1 to 0.1:1.

U.S. Pat. No. 4,873,390 to Lewis et al., incorporated herein by reference, teaches conversion of a feedstock, e.g., alcohols, to a product containing light olefins over a silicoaluminophosphate having pores with diameters of less than 5 Angstroms, wherein carbonaceous deposit material is formed on the catalyst. The catalyst is treated to form a partially regenerated catalyst having from 2 to 30 wt. % of the carbonaceous deposit material, with a preferred range between 4 and 20 wt. %.

U.S. Pat. No. 6,137,022 to Kuechler et al., incorporated herein by reference, discloses a method of increasing selectivity of a reaction to convert oxygenates to olefins by converting the feedstock in a reaction zone containing 15 volume percent or less of a catalyst comprising a silicoaluminophosphate molecular sieve material, and maintaining conversion of the feedstock between 80% and 99% under conditions effective to convert 100% of the feedstock when the reaction zone contains at least 33 volume percent of the molecular sieve material.

U.S. Pat. No. 6,023,005 to Lattner et al., incorporated herein by reference, discloses a method of producing ethylene and propylene by catalytic conversion of oxygenate in a fluidized bed reaction process which utilizes catalyst regeneration. The process maintains a portion of desired carbonaceous deposits on the catalyst (wt. %) by removing only a portion of the total reaction volume of coked molecular sieve catalyst and totally regenerating only that portion of catalyst, which is then mixed back with the unregenerated remainder of catalyst. The resulting catalyst mixture contains 2–30 wt % carbonaceous deposits.

S. Soundararajan et al., "Modeling of methanol to olefins (MTO) process in a circulating fluidized bed reactor", Fuel 80 (2001), 1187–1197 at 1192–93, discuss the effect of coke content (wt. %) on product selectivities from pure methanol using SAPO-34 catalyst. Although a relationship between wt. % carbon on catalyst and selectivity for primary olefins has been observed, it can vary considerably from one catalyst to another, even for molecular sieve materials having the same structure.

Stephen Wilson et al., "The characteristics of SAPO-34 which influence the conversion of methanol to light olefins", Microporous and Mesoporous Materials 29(1999) 117–126, describe the relationship between acid-site strength and density on methanol conversion to light olefins over chabazite structure types (SAPO-34 and SSZ-13) in terms of determining which catalyst was the most resistant to coking at one acid-site per chabazite cage.

Ivar M. Dahl et al., "Structural and chemical influences on the MTO reaction: a comparison of chabazite and SAPO-34 as MTO catalysts", Microporous and Mesoporous Materials 29(1999) 185–190, describe the effect of relationship between acid-site strength and susceptibility of chabazite and SAPO-34 to deactivation for oxygenate conversion at high space velocities to avoid excess catalyst activity causing undesired secondary reactions.

It would be desirable to provide a process for making olefins from oxygenate which maximizes primary olefin yield, especially light olefin yield (ethylene and propylene), for a wide variety of catalysts.

SUMMARY OF THE INVENTION

The present invention relates to a process for making an olefin product from an oxygenate-containing feedstock comprising:

a) contacting the feedstock in a reaction zone with catalyst particles comprising a molecular sieve containing acid sites and having an average coke loading of 1 to 10 carbon atoms per acid site of said molecular sieve, under conditions effective to convert the feedstock into an olefin product stream and to provide unregenerated catalyst particles, b) removing a portion of said catalyst particles from said reaction zone and contacting said portion with a regeneration medium in a regeneration zone under conditions effective to obtain regenerated catalyst particles which have an average coke loading of no greater than 10 carbon atoms per acid site of said molecular sieve, and c) introducing said regenerated catalyst particles into said reaction zone to provide a catalyst mixture of unregenerated catalyst particles and regenerated catalyst particles, in an amount sufficient to provide an average coke loading on said catalyst mixture in an amount ranging from 1 to 10 carbon atoms per acid site of said molecular sieve.

In another embodiment, the present invention relates to the above process which further comprises d) repeating steps a)–c)

In yet another embodiment, the present invention relates to the above process wherein said carbon atoms per acid site is measured using acid site density as determined by NMR.

In still another embodiment, the present invention relates to the above process wherein said oxygenate comprises methanol and said average content of carbon on said catalyst mixture ranges from 1 to 9 carbon atoms per acid site, say, 4 to 7 carbon atoms, of said molecular sieve.

In one embodiment, the present invention relates to the above process wherein said regenerated catalyst particles have an average coke loading of at least 1 and no greater than 10 carbon atoms per acid site, say, an average coke loading of no greater than 2 carbon atoms per acid site.

In yet still another embodiment of the present invention, the above process is carried out in a circulating fluid bed reactor, say, a circulating fluid bed reactor with continuous regeneration.

In still another embodiment of the present invention, the process is carried out wherein the circulating fluid bed reactor is operated at at least 0.2 m/sec superficial gas velocity.

In another embodiment of the above process, the circulating fluid bed reactor is operated at a feedstock conversion between 50% and 99%, say, between 75% and 95%.

In still yet another embodiment of the process, at least a portion of said catalyst mixture exits said reaction zone and is returned to said reaction zone without regeneration.

In yet another embodiment, the present invention comprises a contacting step carried out in a riser.

In another embodiment, the present invention employs a molecular sieve which has a pore diameter of less than 5.0 Angstroms, e.g., a molecular sieve is of a molecular sieve framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted groups thereof. In an alternative embodiment, the molecular sieve is selected from the group consisting of ALPO-18, ALPO-34, SAPO-17, SAPO-18, and SAPO-34.

In another embodiment, the present invention relates to the above process wherein the molecular sieve has a pore diameter of 5–10 Angstroms, e.g., a molecular sieve framework-type which is selected from the group consisting of MFI, MEL, MTW, EUO, MTT, HEU, FER, AFO, AEL, TON, and substituted groups thereof.

In another aspect, the present invention relates to a process for making an olefin product from an oxygenate-containing feedstock comprising:

i) providing an inventory of catalyst particles comprising a molecular sieve containing acid sites, said catalyst particles having an average coke loading of 1 to 10 carbon atoms per acid site of said molecular sieve as measured using acid site density as determined by NMR, ii) contacting the feedstock in a reaction zone with said catalyst particles under conditions effective to convert the feedstock into an olefin product stream to provide unregenerated catalyst particles, iii) removing a portion of said catalyst particles from said reaction zone and contacting said portion with a regeneration medium in a regeneration zone under conditions effective to obtain regenerated catalyst particles having an average coke loading of no greater than 10 carbon atoms per acid site of said molecular sieve, and iv) introducing said regenerated catalyst particles into said reaction zone in an amount sufficient to provide a catalyst mixture of unregenerated catalyst particles and regenerated catalyst particles, said catalyst mixture having an average coke loading of 1 to 10 carbon atoms per acid site on the molecular sieve in said reaction zone.

In one embodiment of this aspect, the process further comprises v) repeating steps ii)–iv).

In another embodiment of this aspect, the catalyst mixture has an average coke loading of 3 to 9 carbon atoms per acid site on the molecular sieve in said reaction zone, and said molecular sieve has a framework-type of at least one selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted groups thereof., e.g., the molecular sieve is selected from ALPO 18, ALPO 34, SAPO 17, SAPO 18, SAPO-34 and substituted groups thereof, say, SAPO 34.

In another aspect, the present invention relates to a process for making an olefin product from an oxygenate-containing feedstock comprising:

A) contacting the feedstock in a reaction zone with catalyst particles comprising a molecular sieve containing acid sites and having no greater than 10 carbon atoms per acid site, under conditions effective to convert the feedstock into an olefin product stream and to provide unregenerated catalyst particles, B) analyzing a portion of said catalyst particles from said reaction zone by measuring the number of carbon atoms per acid site of said molecular sieve using acid site density as determined by NMR, to provide a sample measurement value for said portion, C) contacting a portion of said unregenerated catalyst particles with a regeneration medium in a regeneration zone under conditions, which are a function of said sample measurement value, effective to obtain regenerated catalyst particles which have an average coke loading of no greater than 10 carbon atoms per acid site of said molecular sieve, and D) introducing said regenerated catalyst particles into said reaction zone to provide a catalyst mixture of unregenerated catalyst particles and regenerated catalyst particles, in an amount sufficient to provide an average coke loading on said catalyst mixture ranging from 1 to 10 carbon atoms per acid site of said molecular sieve.

These and other advantages of the present invention shall become apparent from the following detailed description, the attached figure and the appended claims.

DETAILED DESCRIPTION OF THE INVENTION

One goal during the conversion of oxygenates to olefins is to maximize the production of light olefins, preferably ethylene and propylene, and to minimize the production of methane, ethane, propane, and $C_5+$ materials. The present invention maintains the average coke loading of the catalyst in a range particularly selective for producing ethylene and propylene. Such range is based on the acid site density of the molecular sieve component of the catalyst.

Coke levels on the molecular sieve catalyst composition are measured by withdrawing from the conversion process the molecular sieve catalyst composition at a point in the process and determining its carbon content. It is recognized that the molecular sieve catalyst composition in the reaction zone is made up of a mixture of regenerated catalyst and catalyst that has varying levels of carbonaceous deposits. The measured coke level of carbonaceous deposits thus represents an average of the levels of individual catalyst particles.

U.S. Pat. No. 6,023,005, incorporated herein by reference, teaches the desirability of providing carbonaceous deposits, or coke levels, for oxygenates to olefins conversion processes, in the range of 2 wt. % to about 30 wt. % based on the total reaction volume of coked catalyst to promote selectivity to light olefins. However, the inventors have discovered that obtaining particularly preferred results does not consistently depend on maintaining such a coke level range alone, and certainly not over such a wide range as has been previously disclosed. Rather, preferred results in an oxygenate to olefins conversion reaction are in fact a consistent function of the coke level correlated to the particular acidity of the molecular sieve(s) in the catalyst utilized in the conversion reaction. It has now been found that it is advantageous to maintain a average coke loading of the catalyst in a range of 1 to 10 carbon atoms per acid site of the molecular sieve component of the catalyst utilized in an oxygenate to olefins conversion reaction to provide superior prime olefin selectivity.

Molecular Sieves and Catalysts Thereof

Molecular sieves suited to use in the present invention for converting oxygenates to olefins have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types*, 5th edition, Elsevier, London, England (2001), which is herein fully incorporated by reference.

Non-limiting examples of these molecular sieves are the small pore molecular sieves of a framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves of a framework-type selected from the group consisting of AFO, AEL, EUO, HEU, FER, MEL, MFI, MTW, MTT, TON, and substituted forms thereof, and the large pore molecular sieves of a framework-type selected from the group consisting of EMT, FAU, and substituted forms thereof. Other molecular sieves have a framework-type selected from the group consisting of ANA, BEA, CFI, CLO, DON, GIS, LTL, MER, MOR, MWW and SOD. Non-limiting examples of the preferred molecular sieves, particularly for converting an oxygenate containing feedstock into olefin(s), include those having a framework-type selected from the group consisting of AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B.V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing [TO$_4$] tetrahedral units, more preferably, two or more [SiO$_4$], [AlO$_4$] and/or [PO$_4$] tetrahedral units, and most preferably [SiO$_4$], [AlO$_4$] and [PO$_4$] tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. No. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, SAPO$_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

Molecular Sieve Synthesis

The synthesis of molecular sieves is described in many of the references discussed above. Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

In a preferred embodiment the molecular sieves are synthesized by forming a reaction product of a source of silicon, a source of aluminum, a source of phosphorous, an organic templating agent, preferably a nitrogen containing organic templating agent, and one or more polymeric bases. This particularly preferred embodiment results in the synthesis of a silicoaluminophosphate crystalline material that is then isolated by filtration, centrifugation and/or decanting.

Non-limiting examples of silicon sources include a silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E. I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as $ALPO_4$, phosphorous salts, or combinations thereof. The preferred source of phosphorous is phosphoric acid, particularly when producing a silicoaluminophosphate.

Templating agents are generally compounds that contain elements of Group VA of the Periodic Table of Elements, particularly nitrogen, phosphorus, arsenic and antimony, more preferably nitrogen or phosphorous, and most preferably nitrogen. Typical templating agents of Group VA of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium including salts thereof, and tetrabutylammonium including salts thereof, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N', N',N,N-tetramethyl-(1,6) hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2) octane ion; di-n-butylamine, neopentylamine, di-n-pentylamine, isopropylamine, t-butyl-amine, ethylenediamine, pyrrolidine, and 2-imidazolidone.

The preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. The most preferred templating agent is tetraethyl ammonium hydroxide and salts thereof, particularly when producing a silicoaluminophosphate molecular sieve. In one embodiment, a combination of two or more of any of the above templating agents is used in combination with one or more of a silicon-, aluminum-, and phosphorous-source, and a polymeric base.

Polymeric bases, especially polymeric bases that are soluble or non-ionic, useful in the invention, are those having a pH sufficient to control the pH desired for synthesizing a given molecular sieve, especially a SAPO molecular sieve. In a preferred embodiment, the polymeric base is soluble or the polymeric base is non-ionic, preferably the polymeric base is a non-ionic and soluble polymeric base, and most preferably the polymeric base is a polymeric imine. In one embodiment, the polymeric base of the invention has a pH in an aqueous solution, preferably water, from greater than 7 to about 14, more preferably from about 8 to about 14, most preferably from about 9 to 14.

In another embodiment, the non-volatile polymeric base is represented by the formula: $(R-NH)_x$, where (R—NH) is a polymeric or monomeric unit where R contains from 1 to 20 carbon atoms, preferably from 1 to 10 carbon atoms, more preferably from 1 to 6 carbon atoms, and most preferably from 1 to 4 carbon atoms; x is an integer from 1 to 500,000. In one embodiment, R is a linear, branched, or cyclic polymer, monomeric, chain, preferably a linear polymer chain having from 1 to 20 carbon atoms.

In another embodiment, the polymeric base is a water miscible polymeric base, preferably in an aqueous solution. In yet another embodiment, the polymeric base is a polyethylenimine that is represented by the following general formula:

$(-NHCH_2CH_2-)_m[-N(CH_2CH_2NH_2)CH_2CH_2-]_n$, wherein m is from 10 to 20,000, and n is from 0 to 2,000, preferably from 1 to 2000.

In another embodiment, the polymeric base of the invention has a average molecular weight from about 500 to about 1,000,000, preferably from about 2,000 to about 800,000, more preferably from about 10,000 to about 750,000, and most preferably from about 50,000 to about 750,000.

In another embodiment, the mole ratio of the monomeric unit of the polymeric base of the invention, containing one basic group, to the templating agent(s) is less than 20, preferably less than 12, more preferably less than 10, even more preferably less than 8, still even more preferably less than 5, and most preferably less than 4.

Non-limiting examples of polymer bases include: epichlorohydrin modified polyethylenimine, ethoxylated polyethylenimine, polypropylenimine diamine dendrimers (DAB-Am-n), poly(allylamine) [CH$_2$CH(CH$_2$NH$_2$)]$_n$, poly (1,2-dihydro-2,2,4-trimethylquinoline), and poly(dimethylamine-co-epichlorohydrin-co-ethylenediamine).

In another embodiment the invention is directed to a method for synthesizing a molecular sieve utilizing a templating agent, preferably an organic templating agent such as an organic amine, an ammonium salt and/or an ammonium hydroxide, in combination with a polymeric base such as polyethylenimine.

In a typical synthesis of the molecular sieve, the phosphorous-, aluminum-, and/or silicon-containing components are mixed, preferably while stirring and/or agitation and/or seeding with a crystalline material, optionally with an alkali metal, in a solvent such as water, and one or more templating agents and a polymeric base, to form a synthesis mixture that is then heated under crystallization conditions of pressure and temperature as described in U.S. Pat. Nos. 4,440,871, 4,861,743, 5,096,684, and 5,126,308, which are all herein fully incorporated by reference. The polymeric base is combined with the at least one templating agent, and one or more of the aluminum source, phosphorous source, and silicon source, in any order, for example, simultaneously with one or more of the sources, premixed with one or more of the sources and/or templating agent, after combining the sources and the templating agent, and the like.

Generally, the synthesis mixture described above is sealed in a vessel and heated, preferably under autogenous pressure, to a temperature in the range of from about 80° C. to about 250° C., preferably from about 100° C. to about 250° C., more preferably from about 125° C. to about 225° C., even more preferably from about 150° C. to about 180° C. In another embodiment, the hydrothermal crystallization temperature is less than 225° C., preferably less than 200° C. to about 80° C., and more preferably less than 195° C. to about 100° C.

In yet another embodiment, the crystallization temperature is increased gradually or stepwise during synthesis, preferably the crystallization temperature is maintained constant, for a period of time effective to form a crystalline product. The time required to form the crystalline product is typically from immediately up to several weeks, the duration of which is usually dependent on the temperature; the higher the temperature the shorter the duration. In one embodiment, the crystalline product is formed under heating from about 30 minutes to around 2 weeks, preferably from about 45 minutes to about 240 hours, and more preferably from about 1 hour to about 120 hours.

In one embodiment, the synthesis of a molecular sieve is aided by seeds from another or the same framework type molecular sieve.

The hydrothermal crystallization is carried out with or without agitation or stirring, for example stirring or tumbling. The stirring or agitation during the crystallization period may be continuous or intermittent, preferably continuous agitation. Typically, the crystalline molecular sieve product is formed, usually in a slurry state, and is recovered by any standard technique well known in the art, for example centrifugation or filtration. The isolated or separated crystalline product, in an embodiment, is washed, typically, using a liquid such as water, from one to many times. The washed crystalline product is then optionally dried, preferably in air.

One method for crystallization involves subjecting an aqueous reaction mixture containing an excess amount of a templating agent and polymeric base, subjecting the mixture to crystallization under hydrothermal conditions, establishing an equilibrium between molecular sieve formation and dissolution, and then, removing some of the excess templating agent and/or organic base to inhibit dissolution of the molecular sieve. See for example U.S. Pat. No. 5,296,208, which is herein fully incorporated by reference.

Another method of crystallization is directed to not stirring a reaction mixture, for example a reaction mixture containing at a minimum, a silicon-, an aluminum-, and/or a phosphorous-composition, with a templating agent and a polymeric base, for a period of time during crystallization. See PCT WO 01/47810 published Jul. 5, 2001, which is herein fully incorporated by reference.

Other methods for synthesizing molecular sieves or modifying molecular sieves are described in U.S. Pat. No. 5,879,655 (controlling the ratio of the templating agent to phosphorous), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorous modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. patent application Ser. No. 09/929,949 filed Aug. 15, 2001 (cooling molecular sieve), U.S. patent application Ser. No. 09/615,526 filed Jul. 13, 2000 (metal impregnation including copper), U.S. patent application Ser. No. 09/672,469 filed Sep. 28, 2000 (conductive microfilter), and U.S. patent application Ser. No. 09/754,812 filed Jan. 4, 2001 (freeze drying the molecular sieve), which are all herein fully incorporated by reference.

In one preferred embodiment, when a templating agent is used in the synthesis of a molecular sieve, it is preferred that the templating agent is substantially, preferably completely, removed after crystallization by numerous well known techniques, for example, heat treatments such as calcination. Calcination involves contacting the molecular sieve containing the templating agent with a gas, preferably containing oxygen, at any desired concentration at an elevated temperature sufficient to either partially or completely decompose and oxidize the templating agent.

Molecular sieve have either a high silicon (Si) to aluminum (Al) ratio or a low silicon to aluminum ratio, however, a low Si/Al ratio is preferred for SAPO synthesis. In one embodiment, the molecular sieve has a Si/Al ratio less than 0.65, preferably less than 0.40, more preferably less than 0.32, and most preferably less than 0.20. In another embodiment the molecular sieve has a Si/Al ratio in the range of from about 0.65 to about 0.10, preferably from about 0.40 to about 0.10, more preferably from about 0.32 to about 0.10, and more preferably from about 0.32 to about 0.15.

The pH of a reaction mixture containing at a minimum a silicon-, aluminum-, and/or phosphorous-composition, a templating agent, and a polymeric base should be in the range of from 2 to 10, preferably in the range of from 4 to 9, and most preferably in the range of from 5 to 8. The pH can be controlled by the addition of basic or acidic compounds as necessary to maintain the pH during the synthesis in the preferred range of from 4 to 9. In another embodiment, the templating agent and/or polymeric base is added to the reaction mixture of the silicon source and phosphorous source such that the pH of the reaction mixture does not exceed 10.

In one embodiment, the molecular sieves of the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

Method for Making Molecular Sieve Catalyst Compositions

Once the molecular sieve is synthesized, depending on the requirements of the particular conversion process, the molecular sieve is then formulated into a molecular sieve catalyst composition, particularly for commercial use. The molecular sieves synthesized above are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by well-known techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve synthesized above, in a preferred embodiment, is combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include subbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 µm to about 0.6 µm with a D90 particle size distribution of less than about 1 µm.

In one embodiment, the binder, the molecular sieve and the matrix material are combined in the presence of a liquid to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

Upon combining the molecular sieve and the matrix material, optionally with a binder, in a liquid to form a slurry, mixing, preferably rigorous mixing is needed to produce a substantially homogeneous mixture containing the molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve and matrix material, and the optional binder, are in the same or different liquid, and are combined in any order, together, simultaneously, sequentially, or a combination thereof. In the preferred embodiment, the same liquid, preferably water is used. The molecular sieve, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 μm to about 300 μm, preferably from about 50 μm to about 250 μm, more preferably from about 50 μm to about 200 μm, and most preferably from about 65 μm to about 90 μm.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomization fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve in powder form.

Generally, the size of the powder is controlled to some extent by the solids content of the slurry. However, control of the size of the catalyst composition and its spherical characteristics are controllable by varying the slurry feed properties and conditions of atomization.

Other methods for forming a molecular sieve catalyst composition are described in U.S. patent application Ser. No. 09/617,714 filed Jul. 17, 2000 (spray drying using a recycled molecular sieve catalyst composition), which is herein incorporated by reference.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature ranges from about 15 minutes to about 2 hours.

In a preferred embodiment, the molecular sieve catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

Other methods for activating a molecular sieve catalyst composition, in particular where the molecular sieve is a reaction product of the combination of a silicon-, phosphorous-, and aluminum-sources, a templating agent, and a polymeric base, more particularly a silicoaluminophosphate catalyst composition (SAPO) are described in, for example, U.S. Pat. No. 5,185,310 (heating molecular sieve of gel alumina and water to 450° C.), PCT WO 00/75072 published Dec. 14, 2000 (heating to leave an amount of template), and U.S. application Ser. No. 09/558,774 filed Apr. 26, 2000 (rejuvenation of molecular sieve), which are all herein fully incorporated by reference.

Oxygenate to Olefins Process

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or in combination, are converted from a feedstock containing an oxygenate, preferably an alcohol, most preferably methanol, to the preferred olefin(s) ethylene and/or propylene.

One process for converting feedstock into olefins is generally referred to as methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

Increasing the selectivity of preferred hydrocarbon products such as ethylene and/or propylene from the conversion of an oxygenate using a molecular sieve catalyst composition is described in U.S. Pat. No. 6,137,022, and PCT WO 00/74848 published Dec. 14, 2000, which are all herein fully incorporated by reference.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, or a fluidized bed process, preferably a continuous fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in, for example, U.S. Pat. No. 4,076,796, U.S. Pat. No. 6,287,522, and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282, and U.S. patent application Ser. No. 09/564,613 filed May 4, 2000, which are all herein fully incorporated by reference.

In the preferred embodiment, a fluidized bed process or high velocity fluidized bed process includes a reactor apparatus, a regeneration system and a recovery system.

The present invention solves the current needs in the art by providing an improved method for converting a feed including an oxygenate to a product including a light olefin. The method of the present invention is conducted in a reactor apparatus. As used herein, the term "reactor apparatus" refers to an apparatus which includes at least a place in which an oxygenate to olefin conversion reaction takes place. As further used herein, the term "reaction zone" refers to the portion of a reactor apparatus in which the oxygenate to olefin conversion reaction takes place and is used synonymously with the term "reactor." Desirably, the reactor apparatus includes a reaction zone, an inlet zone and a disengaging zone. The "inlet zone" is the portion of the reactor apparatus into which feed and catalyst are introduced. The "reaction zone" is the portion of the reactor apparatus in which the feed is contacted with the catalyst under conditions effective to convert the oxygenate portion of the feed into a light olefin product. The "disengaging zone" is the portion of the reactor apparatus in which the catalyst and any additional solids in the reactor are separated from the products. Typically, the reaction zone is positioned between the inlet zone and the disengaging zone.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably of similar composition, or contain varying proportions of the same or different feedstock with the same or different diluent.

The feedstock entering the fluidized bed reactor apparatus is preferably converted, partially or fully, in the reaction zone into a gaseous effluent that enters the disengaging zone along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging zone, the disengaging zone includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See, for example, U.S. Pat. No. 5,952,538, which is herein fully incorporated by reference.

In another embodiment of the processes for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is a Group IIIA or VIII element from the Periodic Table of Elements) molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001, which is herein incorporated by reference.

The conversion of oxygenates to light olefins is catalyzed by various molecular sieve catalysts. During conversion, carbonaceous deposits known as "coke" unavoidably form on the surface of or within the molecular sieve catalyst. In order to avoid a significant reduction in catalyst activity, the catalyst must be regenerated by burning off coke deposits.

In an embodiment, a portion of the coked molecular sieve catalyst composition is withdrawn from the reactor apparatus and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a coke level less than 0.5 weight percent based on the total weight of the coked molecular sieve catalyst composition, to form a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the regenerated molecular sieve catalyst composition from the regenerator is returned to the reactor apparatus, or directly to the reaction zone, or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

In one embodiment, the cooled regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the reaction zone, directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propanol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are disclosed in U.S. Pat. No. 6,290,916, which is herein fully incorporated by reference.

In one embodiment, the regenerated molecular sieve catalyst composition withdrawn from the regeneration system, preferably from the catalyst cooler, is combined with a fresh molecular sieve catalyst composition and/or recirculated molecular sieve catalyst composition and/or feedstock, and returned to the reactor apparatus. In another embodiment, the regenerated molecular sieve catalyst composition withdrawn from the regeneration system is returned to the reaction zone, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reaction zone.

In one embodiment, the gaseous effluent is withdrawn from the disengaging zone and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, and splitters, and other associated equipment, for example, various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643, U.S. Pat. Nos. 5,019,143, 5,452,581 and 5,082,481, U.S. Pat. No. 5,672,197, U.S. Pat. No. 6,069,288, U.S. Pat. No. 5,904,880, U.S. Pat. No. 5,927,063, and U.S. Pat. No. 6,121,504, U.S. Pat. No. 6,121,503, and U.S. Pat. No. 6,293,998, which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428, U.S. Pat. No. 6,293,999, and U.S. patent application Ser. No. 09/689,363 filed Oct. 20, 2000, which are herein incorporated by reference.

One goal during the conversion of oxygenates to olefins is to maximize the production of light olefins, preferably ethylene and propylene, and to minimize the production of methane, ethane, propane, and $C_5+$ materials. The present invention maintains the average coke loading of the catalyst in a range particularly selective for producing ethylene and propylene. Such range is based on the acid site density of the molecular sieve component of the catalyst.

Coke levels on the molecular sieve catalyst composition are measured by withdrawing from the conversion process the molecular sieve catalyst composition at a point in the process and determining its carbon content. It is recognized that the molecular sieve catalyst composition in the reaction zone is made up of a mixture of regenerated catalyst and catalyst that has varying levels of carbonaceous deposits. The measured coke level of carbonaceous deposits thus represents an average of the levels of individual catalyst particles.

U.S. Pat. No. 6,023,005, incorporated herein by reference, teaches the desirability of providing carbonaceous deposits, or coke levels, for oxygenates to olefins conversion processes, in the range of 2 wt. % to about 30 wt. % based on the total reaction volume of coked catalyst to promote selectivity to light olefins. It further teaches providing a regenerated catalyst having a coke level of less than about 2 wt. % to provide such a total reaction volume of coked catalyst. However, the inventors have discovered that obtaining particularly preferred results does not consistently depend on maintaining such a coke level range alone, and certainly not over such a wide range as has been previously disclosed. It has now been found that it is advantageous to maintain an average coke loading of the catalyst in a range of 1 to 10 carbon atoms per acid site of the molecular sieve component of the catalyst in the reactor apparatus, or more particularly the reaction zone, to provide superior prime olefin selectivity. In various embodiments, the average coke loading on the molecular sieve-containing catalyst utilized in an oxygenate to olefins reaction ranges from 2 to 9, or 3 to 8, or 4 to 7 carbon atoms per acid site of the molecular sieve. A product containing at least about 67.0 wt. %, at least about 70.0 wt. % prime olefins, at least about 72.0 wt. % prime olefins, or even at least about 75.0 wt. % prime olefins can be obtained from the present process. Preferably, a product containing no greater than 4.0 wt. % methane, no greater than 3.0 wt. % methane, or no greater than 2.0 wt. % methane can be obtained from the present process. Additionally, a product containing no greater than 4.0 wt. % propane, preferably no greater than 3.0 wt. % propane, or more preferably no greater than 2.0 wt. % propane can be obtained from the present process.

In order to determine the carbon atoms per acid site of the molecular sieve component of the catalyst it is first necessary to determine the acid site density of the molecular sieve by a suitable analytic method, e.g., by NMR, and then determine the coke content of the catalyst by conventional methods, e.g., by burning off coke to form oxides of carbon which are measured by a suitable analytic method, e.g., IR.

The acid site density of the catalyst can range from 0.10 mmols/g to 0.40 mmols/g of formulated catalyst, e.g., from 0.13 mmols/g to 0.38 mmols/g of formulated catalyst, say, from 0.20 mmols/g to 0.30 mmols/g of formulated catalyst.

The acidity desired for a specific commercial organic conversion catalyst is based upon various factors including the type of the reactor in which conversion takes place, intended operating conditions for the reactor, and feedstock characteristics. Acidity of the catalyst is of particular interest in oxygenates to olefins conversion, inasmuch as excessive acidity can cause premature coking of the catalyst.

For silicoaluminophosphate molecular sieve materials, acidity is typically directly related to the ratio of silicon atoms to aluminum atoms in the framework. Acidity for aluminosilicate molecular sieve materials, e.g, zeolites, is inversely related to the ratio of silicon atoms to aluminum atoms. Thus the desired acidity can be varied for molecular sieve materials by altering synthesis protocols, e.g., by adjusting the ratio of silicon atoms to aluminum atoms in the synthesis mixture. Desired acid site densities for molecular sieve materials can be achieved in other ways as well, including the substitution of a hydrogen ion associated with an acid site with another ion, e.g., metal ion.

A preferred embodiment of a reactor system for the present invention is a circulating fluid bed reactor with continuous regeneration, similar to a modem fluid catalytic cracker.

Because the catalyst must be regenerated frequently, the reactor apparatus should allow easy removal of a portion of the catalyst to a regenerator, where the catalyst is subjected to a regeneration medium, preferably a gas comprising oxygen, most preferably air, to burn off coke from the catalyst, which restores the catalyst activity. The conditions of temperature, oxygen partial pressure, and residence time in the regenerator should be selected to achieve an average coke loading on regenerated catalyst, in various embodiments, of no greater than 10 carbon atoms per acid site, or no greater than 9 carbon atoms per acid site, or no greater than 5 carbon atoms per acid site, or no greater than 2 carbon atoms per acid site, or no greater than 1 carbon atom per acid site of the molecular sieve in the catalyst. At least a portion of the regenerated catalyst should be returned to the reactor apparatus, or more particularly the reaction zone, optionally through some portion of the reactor apparatus or through combination with a recirculated catalyst, described below. In various other embodiments, at least a portion of the regenerated catalyst is returned to the reactor apparatus having an average coke loading of at least 1 and no greater than 10 carbon atoms per acid site, or at least 1 and no greater than 9 carbon atoms per acid site, or at least 2 and no greater than 9 carbon atoms per acid site, or at least 2 and no greater than 8 carbon atoms per acid site.

In an embodiment of the present invention, the reactor apparatus is operated such that a certain average coke loading on the catalyst, comprising a mixture of both regenerated and unregenerated catalyst particles, is maintained in the reactor apparatus, more particularly the reaction zone—an amount such that the molecular sieve-containing catalyst particles in the reactor apparatus or reaction zone have an average coke loading of 1 to 10 carbon atoms per acid site of the molecular sieve, or preferably 2 to 9, or more preferably 3 to 8, or most preferably 4 to 7 carbon atoms per acid site of the molecular sieve.

In one embodiment, the desired average coke loading on the molecular sieve catalyst composition in the reaction zone is maintained by controlling the flow of the regenerated molecular sieve catalyst composition or cooled regenerated molecular sieve catalyst composition from the regeneration system to the reactor system, and regenerator to reactor. Techniques for controlling the flow of a molecular sieve catalyst composition are described in Michael Louge, *Experimental Techniques, Circulating Fluidized Beds*, Grace, Avidan and Knowlton, eds., Blackie, 1997 (336–337), which is herein incorporated by reference.

In one embodiment of the present invention, if the reactor is a high velocity fluidized bed reactor (referred to herein as a riser reactor), above about 2 meters per second gas superficial velocity, then a portion of the catalyst exiting from the disengaging zone is returned, or recirculated, to the reaction zone, becoming recirculated catalyst. This is different from a typical Fluid Catalytic Cracker (FCC) riser reactor, where all or most of the catalyst exiting the top of the reactor and entering the disengaging zone is sent to the regenerator. The return, or recirculation, of coked catalyst directly to the reactor, without regenerating the coked catalyst, allows the average coke level in the reactor to build up to a preferred level. By adjusting the ratio of the flow of the coked catalyst from the disengaging zone to the regenerator and the reactor, a preferred level of carbon atoms per acid site of the molecular sieves of the catalyst particles can be maintained in the reactor apparatus, including on this recirculated catalyst.

In another embodiment of the present invention, if the fluidized bed reactor is designed with low superficial gas velocities, below about 2 m/sec, then cyclones may be used to return catalyst fines to the fluidized bed reaction zone. Such reactors generally have high recirculation rates of solids within the fluidized bed, which allows the coke level on the catalyst to build to a preferred level. Desirable average coke loading can be maintained by withdrawing catalyst from the bed and regenerating the catalyst in the manner described above, and then returning at least a portion of this regenerated catalyst to the reactor.

Figure 1:
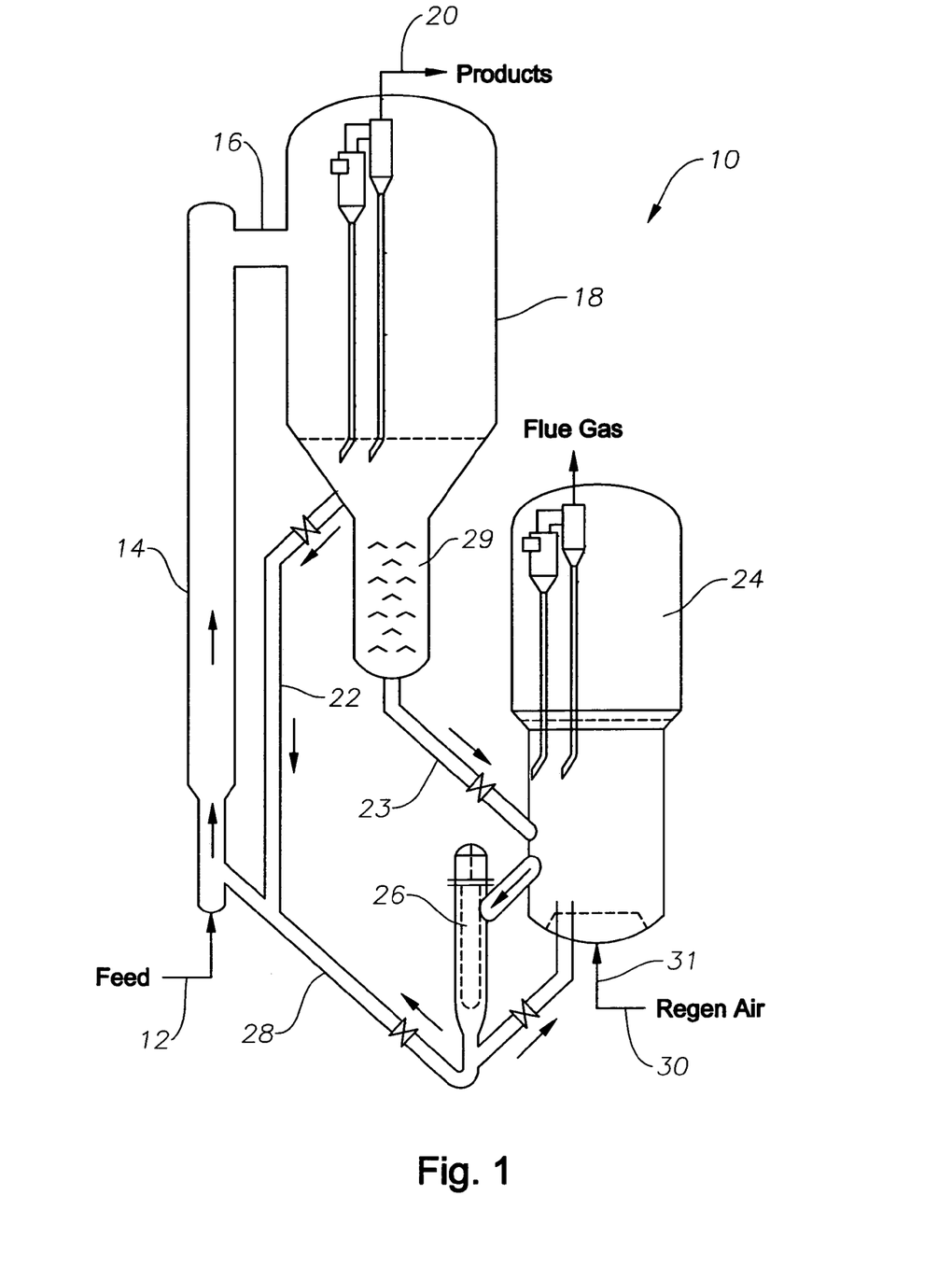
FIG. 1 provides a diagram of a reactor apparatus comprising a high velocity fluid bed with catalyst recirculation, and a regenerator suitable for use in accordance with a preferred embodiment of the present invention.

A preferred embodiment of a reactor apparatus comprising a riser for use in the present invention is depicted generally as 10 in FIG. 1. A methanol feed passed through line 12 is at least partially vaporized in a preheater (not shown). The methanol feed is mixed with regenerated catalyst from line 28 and coked catalyst from line 22 at the bottom of the riser reactor 14. An inert gas and/or steam may be used to dilute the methanol, lift the catalyst streams in line 28, provide fluidization to the catalyst stream in line 22 and keep pressure instrument lines clear of catalyst. This inert gas and/or steam mixes with the methanol and catalyst in the riser reactor 14. The reaction is exothermic, and the preferred reaction temperature, in the range of from about 300° C. to about 500° C., is maintained by removing heat. Heat can be removed by any suitable means, including but not necessarily limited to cooling the reactor with a catalyst cooler (not shown), feeding some of the methanol as a liquid, cooling the catalyst feed to the reactor, or any combination of these methods.

The reactor effluent flowing through the reactor exit 16 of riser reactor 14, containing products, coked catalyst, diluents, and unconverted feed, should flow to a disengaging zone 18. In the disengaging zone 18, coked catalyst is separated from the gaseous materials by means of gravity and/or cyclone separators. A portion of the coked catalyst in line 22 is recirculated to the reactor inlet at the bottom of riser reactor 14. The portion of coked catalyst from line 22 to be regenerated is first sent to a stripping zone 29, where steam or other inert gas is used to recover adsorbed hydrocarbons from the catalyst. Stripped spent coked catalyst via line 23 flows to the regenerator 24. The portion of the catalyst sent to the regenerator 24 should be contacted with a regeneration medium, preferably a gas comprising oxygen via line 30 introduced through regeneration medium inlet 31, at temperatures, pressures, and residence times that are capable of burning coke off of the molecular sieve-containing catalyst and down to a level of no greater than 10 carbon atoms, say less than 3, 2, or even 1 carbon atom(s) per acid site of the molecular sieve.

The preferred temperature in the regenerator is in the range of from about 550° C. to about 700° C., the preferred oxygen concentration in the gas leaving the regenerator is in the range of from about 0.1 vol % to about 5 vol %, and the preferred residence time is in the range of from about 1 to about 100 minutes.

The burning off of coke is exothermic. The temperature may be maintained at a suitable level by any acceptable method, including but not limited to feeding cooler gas, cooling the catalyst in the regenerator with a cat cooler 26, or a combination of these methods.

The regenerated catalyst is sent via line 28 to the reactor 14, where it mixes with the recirculated coked catalyst from line 22 and the methanol feed from line 12. The regenerated catalyst in line 28 may be lifted to the reactor 14 by means of an inert gas, steam, or methanol vapor introduced via a lift gas line (not shown). The process should repeat itself in a continuous or semi-continuous manner. The hot reactor product gases exiting via line 20 should be cooled, the water byproduct condensed and collected, and the desired olefin product gases recovered for further processing.

In order to determine the loading of coke in the reactor and/or in the regenerator, small aliquots of catalyst may be continuously or periodically withdrawn or directly sampled from an appropriate point or points in the reactor apparatus, e.g., the reaction zone or disengaging zone or any catalyst recirculation pathway present (exclusive of the regenerated catalyst pathway). In one embodiment, the catalyst recirculation pathway can be defined as the path through riser 14 through line 16 to the disengaging zone 18 thence through line 22, returning via line 28 to the riser 14.

In an embodiment of the present invention, coke level can be determined by IR measurement of oxides of carbon produced by combustion of coke on catalyst. Average coke loading in terms of carbon atoms per acid site on the molecular sieve of the catalyst is then determined from the coke level by reference to determination of acid sites in the molecular sieve by a suitable technique, e.g., NMR determination of acid site density as described below. The process controls may be adjusted accordingly to provide desired average coke loading, e.g., by controlling the amount of addition of regenerated catalyst from the regeneration zone to the reaction zone, and/or the extent to which coke is removed during regeneration.

The following examples illustrate, but do not limit, the present invention.

EXAMPLE 1

SAPO-34 was prepared in accordance with the method set out in U.S. Pat. No. 4,440,871 to Lok, incorporated herein by reference. Two different samples with slightly different acid densities were prepared. Catalyst One contained a molecular sieve which was an intergrowth of SAPO-34 and SAPO/ALPO-18 and had an acid density of 0.13 mmoles $H^+$/g formulated catalyst. Catalyst Two, containing a nearly pure SAPO-34, had a higher acid density of 0.38 mmoles $H^+$/g formulated catalyst. Acid density was measured by magic angle spinning solid state proton NMR in accordance with the procedure set out below.

Acid Site Density Measurement

Sample Preparation for NMR measurements: Prior to the NMR measurements, SAPO-34 samples were calcined in air at 650° C., packed in 4 mm (o.d.) $ZrO_2$ Bruker MAS rotors, evacuated at 400° C./10 hrs, then capped under $N_2$.

Experimental NMR Parameters: 360.13 MHz $^1$H MAS NMR spectra were obtained on the Bruker AMX360 wide bore spectrometer with a 4 mm MAS probe using 10.0 kHz spinning, 3.0 μs 90° pulses, a 30 s pulse delay, and 32 scans were collected. The absolute amount of H in each sample was determined by directly comparing the experimental spectral area relative to that of the quantitation standard and weight normalizing. The standards and the samples were run back to back under identical conditions to minimize any effects due to the spectrometer instability. The spectrometer tuning was not changed from sample to sample, or from sample to standard. A full rotor of octakis(trimethylsiloxy) silesquioxane, more commonly known as Q8M8, available from Strem Chemicals (CAS#51777-38-9) was used as the external quantitation standard. It is a solid at room temperature, has similar tuning characteristics to SAPOs, and has one peak at about 0.3 ppm from TMS. Measurements done in quadruplicate on similar systems gave a standard deviation of <4% for this methodology.

Average Coke Loading Measurement

Coke level was measured with a LECO analyzer, Model C-200. The analyzer essentially burns the carbonaceous species and analyzes the off gas. By dividing the amount of carbon observed in the off gas by the weight of the sample analyzed, the carbon loading on the catalyst as a percentage is determined. Any other chemicals (e.g., hydrogen) not observed with the LECO analyzer were assumed to be absent for the purposes of the discussion herein and are therefore not included quantitatively as coke level.

When performing a coke level measurement, the crucible and crucible lid were removed from a nitrogen-purged dry box. Approximately 0.8 grams of iron chip accelerator and 1.3 grams of copper accelerator (both supplied by LECO Corporation) were blended in the crucible with roughly 0.2 grams of catalyst. Zero grade oxygen which had been filtered by an anhydrone (magnesium perchlorate, supplied by LECO) and a $CO_2$ absorber (sodium hydroxide on a non-fibrous silicate carrier, also from LECO) were passed over the heated catalyst sample. The catalyst was heated with an induction furnace. CO and $CO_2$ were evolved and passed through the anhydrone and were then sent through a bed of platinum on alumina obtained from LECO. This bed oxidized all the CO to $CO_2$. The resulting gas was passed through an infrared detector where $CO_2$ was detected. The IR detector was calibrated using two standard samples—3.31 wt. % carbon (carbon and sulfur in white iron, supplied by LECO) and 6.17 wt. % carbon (tungsten carbide, also from LECO).

The mass of carbon detected by the IR cell was divided by the catalyst weight to determine the coke level as a percentage. Knowing the acid site density by the NMR method detailed above in units of moles of acid sites per gram formulated catalyst and coke level as grams coke per gram formulated catalyst, carbon molecules per acid site (i.e., average coke loading) were determined as: C atoms/site= (coke level [g/g])/(molecular weight [g/mol])/(acid density [moles/g]). The number of carbon atoms per site was an average across all the particles in the sample.

Methanol to olefin experiments were conducted in a fluidized bed reactor as set out in FIG. 1 where distilled methanol was reacted with formulated SAPO-34 catalyst. Methanol, fed mostly as a vapor, contacted the catalyst cocurrently at the bottom of the reactor. The energy of the gas due to its velocity carried the catalyst out of the riser and into a cyclone train. The gas was separated from the catalyst in the cyclones. At the solids discharge from the cyclone, most of the catalyst was recirculated to the reactor again while a small portion (about 5%) was sent to a regenerator. Coke on the catalyst was burned to reactivate the catalyst. The regenerated catalyst was then returned to the reactor catalyst recirculation loop. The average coke loading on the catalyst in the riser was controlled by regeneration conditions.

The experiments were conducted at constant pressure, temperature, and conversion with varying average coke loading. As the average coke loading increased, catalyst reactivity to methanol decreased. Therefore, space velocity was varied simultaneously with average coke loading such that conversion at the outlet of the reactor was held constant. More precisely, the space velocity was decreased as average coke loading was increased so that total reactor activity was held constant. Coke level is reported as (1) the mass of carbon divided by the total mass of catalyst and (2) average coke loading is reported as the average number of carbon atoms deposited divided by the number of catalytic acid sites. Coke deposition was measured by burning off the carbon from a reactor catalyst sample and measuring the amount of $CO_x$ that evolved using a LECO Model C-200. For each test, conditions were held constant at 98% reactor outlet conversion in the reactor, 488° C. average riser temperature and 276 kPa (25 psig) riser outlet pressure. Space velocity was reported as the ratio of methanol feed to (1) the mass of catalyst in the riser and (2) the number of acid sites in the reactor. A summary of the test results is set out in Table 1 below.

TABLE 1

| | Units | Test 1 | Test 2 | Test 3 | Test 4 |
|---|---|---|---|---|---|
| Catalyst | — | 1 | 1 | 1 | 2 |
| Carbon on formulated catalyst | wt. % | 7.98 | 5.15 | 3.94 | 4.86 |
| Sieve content of catalyst | wt. % | 0.4 | 0.4 | 0.4 | 0.4 |
| Acid site density | mmol H+/g formulated catalyst | 0.13 | 0.13 | 0.13 | 0.38 |
| Carbon on sieve | wt. % | 20.0 | 12.9 | 9.9 | 12.2 |
| Carbon per acid site | C atoms/acid site | 10.5 | 6.8 | 5.2 | 2.1 |
| Conversion* | wt. % | 98.0 | 98.3 | 97.7 | 97.9 |
| SV (1) | hr-1 | 1.3 | 2.6 | 11.1 | 73.0 |
| SV (2) | lb MeOH/h/mole acid site | 20.5 | 40.9 | 174.6 | 382.8 |
| C1** | wt. % | 4.3 | 2.7 | 1.4 | 1.0 |
| C2= | wt. % | 33.7 | 35.8 | 34.6 | 33.4 |
| C2o | wt. % | 1.0 | 0.8 | 0.8 | 0.9 |
| C3= | wt. % | 33.2 | 36.4 | 37.7 | 38.0 |
| C3o | wt. % | 1.5 | 1.1 | 1.4 | 3.6 |
| C4s | wt. % | 11.5 | 12.1 | 12.9 | 11.4 |
| C5+ | wt. % | 6.7 | 6.2 | 7.9 | 5.8 |

TABLE 1-continued

| | Units | Test 1 | Test 2 | Test 3 | Test 4 |
|---|---|---|---|---|---|
| Coke | wt. % | 8.1 | 4.8 | 3.3 | 5.9 |
| C2=+C3= | wt. % | 66.9 | 72.2 | 72.3 | 71.3 |

*Conversion was calculated by formula: Conv. = 100 − (14/32) × (wt. % MeOH) − (30/46) × (wt. % DME)
**Selectivities were calculated on a dry (water-free) basis The data of Table 1 are set out in FIGS. 2 to 5.

Figure 2:
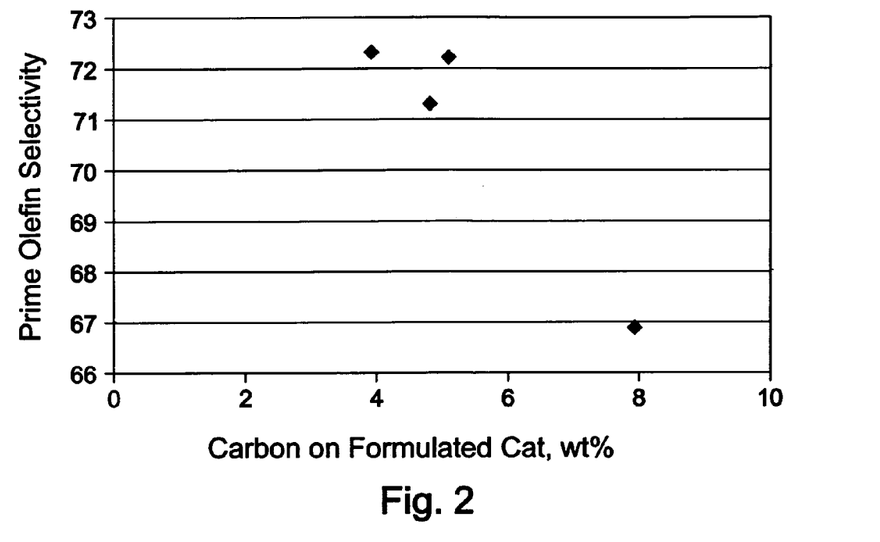
FIG. 2 depicts prime olefin selectivity versus carbon on catalyst by weight in a methanol to olefins conversion process of a preferred embodiment of the present invention.

FIG. 2 depicts prime olefin selectivity versus carbon on the catalyst. FIG. 2 shows that no consistent trend is apparent for prime olefin selectivity at different coke levels measured on the basis of formulated catalyst.

Figure 3:
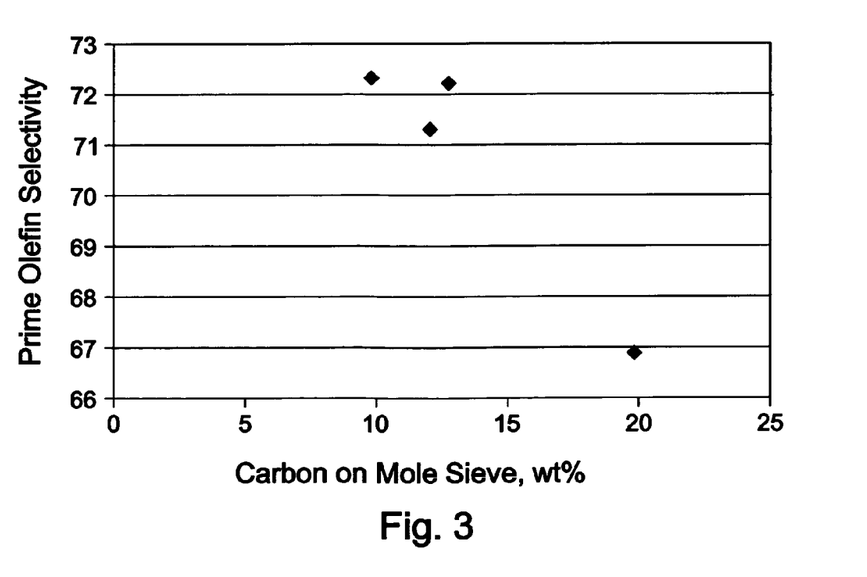
FIG. 3 depicts prime olefin selectivity versus carbon on the molecular sieve by weight in a methanol to olefins conversion process of a preferred embodiment of the present invention.

FIG. 3 depicts prime olefin selectivity versus carbon on the molecular sieve. FIG. 3 also shows that no consistent trend is apparent in prime olefin selectivity at different coke levels measured on the basis of molecular sieve.

Figure 4:
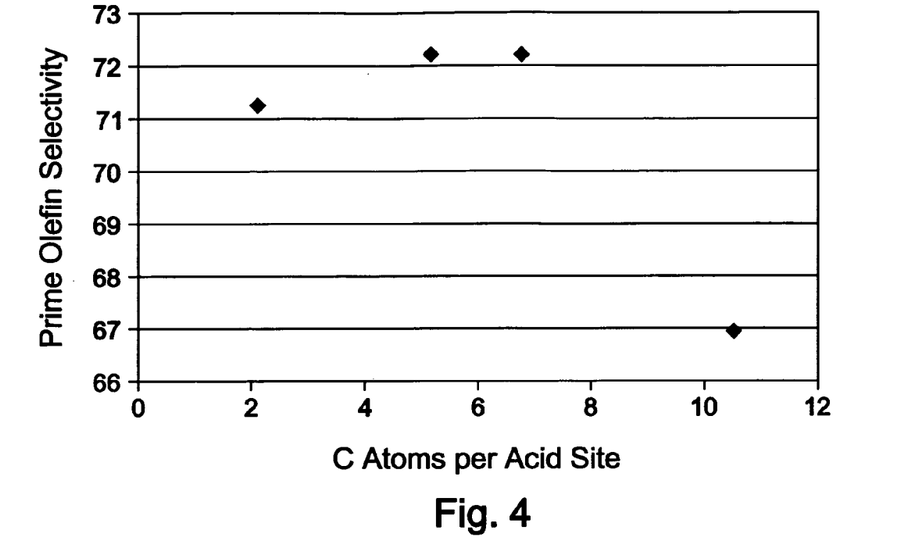
FIG. 4 depicts prime olefin selectivity versus carbon atoms per acid site in a methanol to olefins conversion process of a preferred embodiment of the present invention.

FIG. 4 depicts prime olefin selectivity versus carbon atoms per acid site. FIG. 4 shows a consistent trend with a clearly defined maximum region for prime olefin selectivity at different average coke loadings (measured on the basis of acid sites associated with molecular sieve).

Figure 5:
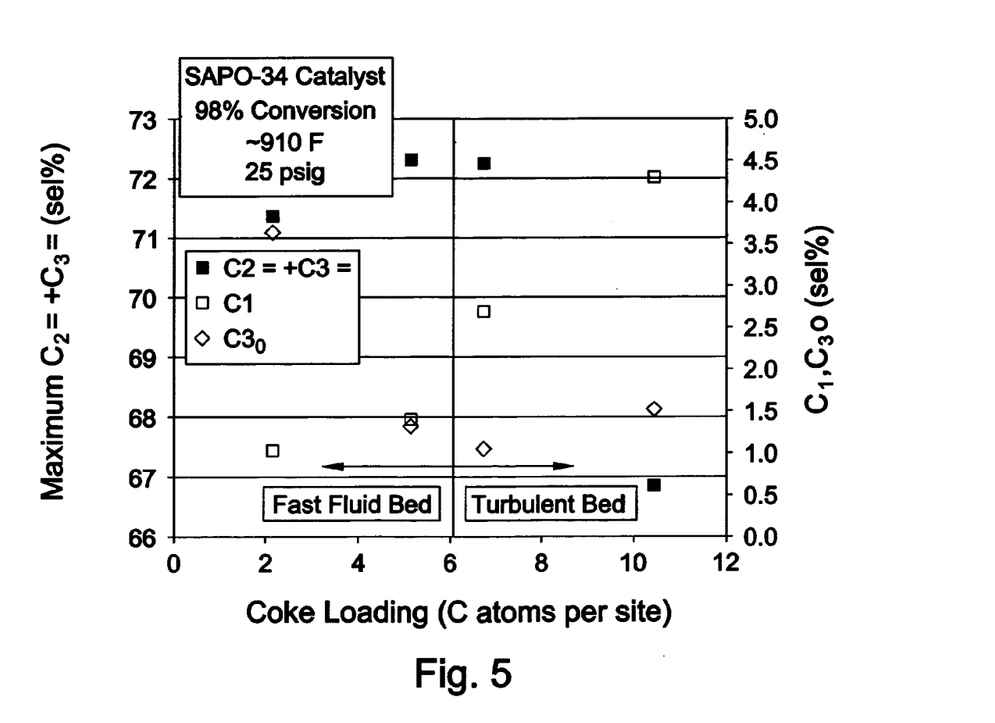
FIG. 5 depicts prime olefin selectivity, methane selectivity and propane selectivity versus carbon atoms per acid site and shows a well-defined maximum light olefin selectivity as a function of average coke loading in a methanol to olefins conversion process of a preferred embodiment of the present invention.

FIG. 5 depicts prime olefin selectivity, methane selectivity and propane selectivity versus carbon atoms per acid site and shows a well-defined maximum light olefin selectivity as a function of average coke loading. One skilled in the art relying solely upon coke level of the catalyst clearly would be at a significant disadvantage in deriving ranges of operation which provide maximum levels of prime olefin selectivity in oxygenate to olefin conversion.

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

The invention claimed is:

1. A process for making an olefin product from an oxygenate-containing feedstock comprising:
   a) contacting the feedstock in a reaction zone with catalyst particles comprising a molecular sieve containing an average density of acid sites of about 0.000325 mole per gram of said molecular sieve and having an average amount of carbon on said molecular sieve ranging from about 9.9 wt.% to about 12.9 wt.% based on the weight of the molecular sieve, wherein said average density of acid sites is is determined by NMR, under conditions effective to convert the feedstock into an olefin product stream and to provide unregenerated catalyst particles,
   b) removing a portion of said unregenerated catalyst particles from said reaction zone and contacting said portion with a regeneration medium in a regeneration zone under conditions effective to obtain regenerated catalyst particles wherein said average amount of carbon on said molecular sieve of said regenerated catalyst particles is no greater than 9.9 wt.% based on the weight of said molecular sieve, and
   c) introducing said regenerated catalyst particles into said reaction zone.

2. The process of claim 1 which further comprises
   d) repeating steps a)–c).

3. The process of claim 1 which is carried out in a circulating fluid bed reactor.

4. The process of claim 1 which is carried out in a circulating fluid bed reactor with continuous regeneration.

5. The process of claim 1 wherein said regenerated catalyst particles have an average coke level of at least 3.94 wt.% based on the weight of the unregenerated catalyst particles.

6. The process of claim 3 wherein said circulating fluid bed reactor is operated at at least 0.2 m/sec superficial gas velocity.

7. The process of claim 6 wherein said contacting is carried out in a riser.

8. The process of claim 3 wherein said circulating fluid bed reactor is operated at a feedstock conversion between 50% and 99%.

9. The process of claim 3 wherein said circulating fluid bed reactor is operated at a feedstock conversion between 75% and 95%.

10. The process of claim 1 wherein at least a portion of said catalyst mixture exits said reaction zone and is returned to said reaction zone without regeneration.

11. The process of claim 1 wherein said molecular sieve has a pore diameter of less than 5.0 Angstroms.

12. The process of claim 11 wherein said molecular sieve framework-type is selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted groups thereof.

13. The process of claim 12 wherein said molecular sieve is selected from the group consisting of ALPO-18, ALPO-34, SAPO-17, SAPO-18, and SAPO-34.

14. The process of claim 12 wherein said molecular sieve is SAPO-34.

15. The process of claim 1, wherein said molecular sieve has a pore diameter of 5–10 Angstroms.

16. The process of claim 15 wherein said molecular sieve framework-type is selected from the group consisting of MFI, MEL, MTW, EUO, MTT, HEU, FER, AFO, AEL, TON, and substituted groups thereof.

* * * * *